(12) United States Patent
Herlik (10) Patent No.: US 6,354,152 B1
(45) Date of Patent: Mar. 12, 2002

(54) METHOD AND SYSTEM TO MEASURE DYNAMIC LOADS OR STRESSES IN AIRCRAFT, MACHINES, AND STRUCTURES

(76) Inventor: Edward Charles Herlik, 456 H W. Rockrimmon Blvd., Colorado Springs, CO (US) 80919

(*) Notice: Subject to any disclaimer, the term of this patent is extended or adjusted under 35 U.S.C. 154(b) by 0 days.

(21) Appl. No.: 09/450,116

(22) Filed: Nov. 26, 1999

Related U.S. Application Data (63) Continuation-in-part of application No. 08/852,684, filed on May 7, 1997, now abandoned.
(60) Provisional application No. 60/016,591, filed on May 8, 1996.

(51) Int. Cl.[7] ............................................... G01N 29/00
(52) U.S. Cl. .............................. 73/597; 73/597; 73/802
(58) Field of Search ......................... 73/761, 772, 778, 73/786, 597, 629, 862.59, 771, 802

(56) References Cited

U.S. PATENT DOCUMENTS

| | | | |
|---|---|---|---|
| 3,969,960 A | * 7/1976 | Pagano | 73/761 |
| 4,294,122 A | 10/1981 | Couchman | |
| 4,295,377 A | 10/1981 | Couchman | 73/761 |
| 4,601,207 A | 7/1986 | Steblay | 73/761 |
| 4,899,591 A | 2/1990 | Kibblewhite | 73/761 |
| 5,131,276 A | 7/1992 | Kibblewhite | 73/761 |
| 5,220,839 A | 6/1993 | Kibblewhite | |
| 5,381,005 A | 1/1995 | Chazelas et al. | |
| 5,511,430 A | * 4/1996 | Delest et al. | 73/802 |
| 5,569,857 A | 10/1996 | Miyazaki | |
| 5,699,159 A | 12/1997 | Mason | |
| 5,905,212 A | 5/1999 | Moses et al. | |
| 5,942,750 A | 8/1999 | Sannerhaugen et al. | |
| 5,969,260 A | 10/1999 | Belk et al. | |
| 5,970,798 A | 10/1999 | Gleman et al. | |
| 5,973,273 A | 10/1999 | Tal et al. | |

* cited by examiner

Primary Examiner—John E. Chapman (57) ABSTRACT

The system and method of this invention determines stress within the load bearing members of an aircraft, machine or structure in order to improve their design, safety and efficiency as well as enhancing their operation. Load or stress is calculated from signals generated in fasteners fitted with piezoelectric crystals. Rather than indirect stress indication through approximations from accelerometers, optical fibers, position sensors, strain gages and the like, this invention calculates load or stress from sensors installed directly into load bearing elements. This invention can perform stress indicating function in machines and structures such as, but not limited to, aircrafts, buildings, bridges, power generating stations, ships and engines.

20 Claims, 7 Drawing Sheets

METHOD AND SYSTEM TO MEASURE DYNAMIC LOADS OR STRESSES IN AIRCRAFT, MACHINES, AND STRUCTURES

This application is a continuation in part of Ser. No. 08/852,684, filed May 7, 1997 abandoned, and this application claims the benefit of U.S. Provisional application No. 60/016,591, filed May 8, 1996.

BACKGROUND OF THE INVENTION

1. Field of the Invention

Structural stress measurements are critical to aircraft and many other structures. Overstressed members require expensive inspections at best and can fail in flight at worst. Uncertainty about actual loads borne by structural members forces aircraft designers to increase the mass of critical parts as a safety margin. That increased mass reduces the aircraft's performance while increasing stress on other structural members. Typically static structures such as bridges, dams and buildings must be designed for external loads imparted by earthquake, wind and even sunlight. Severe external loads, such as those imparted by turbulence on an aircraft or earthquake on a bridge, require expensive and time consuming inspections before the machine or structure can be returned to service. The art of determining loads has attempted to reduce that uncertainty with a myriad of external sensors overlaid on structures. Those external sensors are separate, expensive systems which require precision attachments and calibration. None of them is capable of actually measuring internal loads in structural members so each measures an external strain, position or even optical characteristic in order to estimate internal stress.

2. Description of the Related Art

One of the many attempts to measure stress or loads in structures is illustrated in U.S. Pat. No. 5,381,005 by Chazelas and Turpin. Their Optical Fiber Stress Detector Using Amplitude Modulation is a variation on fiber optic detectors which are overlaid on or embedded in structural elements. While functional, such overlaid systems all share the limitations of any system which adds complexity, cost and weight while not contributing to a structure's function. The present invention avoids most of those problems by using functioning fasteners as sensors where possible.

Optical sensors are common in this art for their precision and non-metallic composition. The present invention's primary function is determining dynamic loads in aircraft and other structures while in operation. That function is met for ships with the optical sensors described in U.S. Pat. No. 5,942,750 Method and Device for Continuous Monitoring of Dynamic Loads by Sannerhaugen and Hellvik. As is always the case in the art, '750 teaches an externally applied apparatus of sensors overlaid on the structure. Optical strain sensors are rigidly attached to a ships hull and connected by fiber optic cable to the processing means. The entire cost of this system is added to the structure's cost while many potential failure points are evident, such as the security of each strain sensor's attachment.

Another variation on this theme is seen in U.S. Pat. No. 5,569,857 Vehicle Stress Detecting and Measuring Method and Stress Detecting Device Using said Method by Miyazaki. That inventor isolated the shear vector from various forces within a structural member by, again, using external sensors applied with the typical drawbacks.

An example of the extremes reached in attempting to determine stress in structural members is seen in U.S. Pat. No. 5,699,159 Loadmeter Employing Birefringence to Measure Mechanical Loads and Stresses by Mason. His invention is interesting in that loads are calculated without physical contact with the member. In addition to the other problems inherent in applying an external measurement system, it requires the added complexity of a "birefringent coating" on the member with cameras and computers equipped to evaluate the "spectral demodulation".

Various strain gages are also common in the art. The present invention is capable of calculating the external loads on a member or part through knowledge of the loads or stresses resulting within that part. Moses and Hogan meet the same need using strain gages in U.S. Pat. No. 5,905,212 Load and Deflection Measurement System for Elastomeric Bearings. Once again, conventional devices such as the "metal foil strain gages" are applied to the outside of the member in order to indirectly determine the relevant forces. Those external sensors require precision application and maintenance while only estimating the internal loads.

There are several interesting variations on the external sensor theme. One objective of the present invention is detecting cracks. That need is addressed by Belk and White in U.S. Pat. No. 5,969,260 Remotely Interrogatable Apparatus and Method for Detecting Defects in Structural Members. As with the rest of the art, the Belk et al invention requires the overlay of a sensing system on the structural member in question; in this case a wire is incorporated in composite structures. While functional, it includes further limits such as one-time operation (since breaking the detection circuit renders it inoperative), no warning before an overload causes the member to fail or crack, and intermittent operation available only when a technician connects more hardware to the detection device. The present invention meets the same need with none of these limitations.

Position sensing is also used to estimate loads. Another objective of the present invention is determining the payload weight and distribution of a vehicle. This objective is also attempted in U.S. Pat. No. 5,973,273 Method for Determining Weight of a Vehicle in Motion by Tal and Elad. Once again, limitations of the art are severe. '273 teaches measuring the deflection of vehicle axles with conventional, external sensors in order to infer the weight borne by them. That method only works when the vehicle is in motion and only if the characteristics of the springs are know with precision. The present invention would serve the same purpose by measuring the load inside relevant structures at rest or in motion and with no need to know the characteristics of the vehicle's suspension.

The advantages over all such externally applied conventional sensors are many.

An art previously unrelated to this subject of measuring internal structural stresses is that of setting the torque on a fastener. Safe and reliable joints require fasteners installed to the proper torque. This art includes mechanical devices such as torque wrenches or indicating pins mounted on fasteners which move as torque is applied. More precision is possible through he use of ultrasonic transceivers to measure the time of flight of a sound pulse, i.e. a bolt's length, as it elongates during tightening. That technique of setting torque on a bolt by measuring elongation with ultrasonics is well known and, while certainly possible with the present invention, is not an object of this invention. An important segment of this unrelated torquing art is the development of fasteners containing piezoelectric crystals permanently embedded within.

The torquing art with the aid of ultrasonics is summarized in Fastener Incorporating Ultrasonic Transducer U.S. Pat. No. 4,294,122 by Couchman. He teaches providing fasteners modified with permanent transducers for actively measuring preloads on those fasteners using ultrasonic signals. His modified fastener incorporates an acoustic transducer permanently anchored in an opening formed in its head. Fasteners such as that described by Couchman '122 are required for the present invention. His stated objective is, ". . . to obtain more accurate preloading measurements and also to provide for improved quality control inspection of the fastener and to allow acoustic monitoring of critical fasteners." with the sensing tool temporarily pressed against the surface of the fastener. In other words, he developed a method for measuring the preload torque in fasteners and then rechecking that torque on occasion. Here again, the inventor's sole emphasis is on the binding force exerted by the fastener on the materials which it binds.

In the related patent Fastener Incorporating Removable Ultrasonic Transducer U.S. Pat. No. 4,295,377, Couchman repeats his points from '122 while incorporating a "transducer (which) may be removed for repair or replacement purposes.". Improved acoustic contact in order to accurately determine the torque on a fastener is the objective; though his removable transducer would not function in the present invention. Couchman '377 does take measuring preload one step further with, ". . . as well as subsequent measurements to detect for flaws or cracks or which may be employed subsequently for monitoring purposes.". This inventor makes it clear that his intent is to improve the fastener torquing art with provisions for occasionally rechecking that torque, as well as checking fastener integrity by detecting cracks in said fasteners, while temporarily pressing the "removable ultrasonic transducer" against the individual fastener in question. In both '122 and '377, Couchman also provides detailed work on such ultrasonic fasteners themselves and the circuitry required to interrogate them. As with other inventions in the torquing art, these are not concerned with dynamic loads during operation of the structure.

Couchman '377 states that "One may use the embodiments of FIGS. 2–4 (i.e. the bolt) to look for acoustic emissions or for other diagnostic purposes while the vehicle is in operation or flight and which may result from bolt or adjacent structural failure." By itself, that sentence seems to imply a function similar to the present invention. But that paragraph continues with, "In this embodiment, the pulser 121 will NOT be employed. The output of the transducer will be coupled to circuits 127, 129, and 131 and the output of circuit 131 will be monitored. FIG. 6 illustrates one way in which ACOUSTIC EMISSIONS, which may occur while the vehicle is in operation or in flight due to bolt or adjacent structural failure, may be monitored. The embodiment of FIG. 2 is shown in this figure. The system 93 will have a suitable readout for monitoring for acoustic emissions from the bolt or from the adjacent structure." (Capitalization added for emphasis). Couchman is saying that his bolt may be used, with the ultrasonic signal generating system disconnected, as a microphone. If the bolt or surrounding structure breaks and thereby makes noise, his invention can hear it. That in no way implies an ability to figure out how many kilo Newtons of force the wing structure bears which is an example of the present invention's use.

Well known piezoelectric or ultrasonic fasteners are described in the Couchman patents and also by Kibblewhite who authored a series of patents, culminating in U.S. Pat. No. 5,220,839 Ultrasonic Load Measuring Device with Control Feature, which teach improvements in the art of constructing fasteners incorporating piezoelectric media. Such fasteners are not claimed in this invention and would be purchased on the open market for use both in their anticipated function as precision fasteners and their unanticipated function or new use herein as sensors. While Kibblewhite uses similar terms with statements such as, "Yet another object of the present invention is to provide a method and an apparatus for reliably and removably coupling a load measuring device with a load indicating member or fastener and for repeatedly or continuously monitoring the load indicating member or fastener.", his invention is distinct. In context, it is clear that Kibblewhite and Couchman both invented variations on ultrasonic bolts, nothing more. "Continuous" to them means that a properly equipped wrench may interrogate their fasteners "continuously" while turning it. The wrench must then be removed in order for the machine or structure containing their fastener to operate. This point is reinforced by the first line of the first claim in a Kibblewhite patent, "A method of making a load indicating fastener . . . ".

A critical point, at the heart of the present invention, is that fasteners and other fittings, equipped with transceivers, function in entirely new use as sensors. In this new use, modified fittings are able to measure stress or loads inside the structural members into which they are installed. They perform this new use regardless of whether or not they perform other functions such as securing joints, suspending loads or reinforcing a structure. All previous ultrasonic fastener art has been solely concerned with measuring load within a fastener and does not teach or anticipate determining stress or load in a machine or structure. Even though a fastener may also be defined as a member of a machine or structure, it must be understood that the acoustic fasteners invented by Couchman, Kibblewhite and others are used here as sensors installed in structural members such as aircraft wings. Understood properly, it is obvious that such fasteners are to structural members as thermometers are to the human body. The fact that acoustic fasteners may also form joints speaks to the efficiency of the present invention but is not necessary to the fastener's function as a sensor.

The most interesting application of ultrasonic measurement technology to fasteners is seen in the recent patent U.S. Pat. No. 5,970,798 Ultrasonic Bolt Gage by Gleman and Rowe for NASA. As with others working to improve the art of torque measurement, they are concerned only with the preload on critical fasteners which must join structural members with the precision and reliability required by the space program. Gleman and Rowe '798 improves the torquing art by satisfying that preload measurement requirement with a multiplexing arrangement that allows more than one fastener to be interrogated during a test, albeit only one at a time. Their connection and interrogation method would not work for the present invention, however, as Gleman and Rowe '798 teaches a temporary connection to the fasteners, an ultrasonic transceiver mounted in the test system rather than in the fastener (so as to not lose the transceivers on launch) plus interrogating those fasteners one at a time. The Gleman and Rowe '798 patent, which discloses a multiplexed system using ultrasonics to determine the torque on multiple fasteners, fails to mention any possibility of permanent attachments at the fasteners; or measuring any load beyond that inside the fastener; or any possibility of determining loads within the structure in operation (during launch for Gleman and Rowe '798); or any possibility that monitoring the loads at fastener locations could contribute to the safety and operation of the structure. All of those advantages and more are obtained by the present invention.

The present invention works regardless of whether or not the piezoelectric equipped fasteners are also used to form joints. One possible application illustrating that versatility is U.S. Pat. No. 5,970,679 Metal Load bearing Structure having Structural Connections with no Welding or Drilling by Amore. As the title says, this invention creates a load-bearing structure with no fasteners. The present invention allows piezoelectric equipped fasteners to be installed at any relevant location to determine the stresses within such a structure in spit e of no joining function for the fastener.

SUMMARY OF THE INVENTION

This invention relates to measuring static or dynamic stress in the load bearing members of aircraft and other structures or machinery. More specifically, it relates to taking such measurements from sensors located directly inside the load bearing member in question rather than inferring the stresses from indirect measurements. The current art estimates such stress through indirect indicators such as strain gages (which measure stress in the gage and infer the stress in the associated member) and accelerometers (which measure acceleration experienced by the meter and infer conditions within the associated machine). This invention also addresses detecting failures in load bearing members, such as cracks and failed fasteners, which must now be detected with manual inspections often requiring purpose built Non-Destructive Inspection hardware and costly down time. The innovative sensors proposed for this new method are fasteners equipped with piezoelectric crystals or other means for ultrasonic measurement. The present invention is applicable regardless of the material comprising the structural member such as metal, composite, wood or plastic.

Currently, unreliable fasteners and fastener torque settings require over-engineering for safety with the associated weight, cost and performance penalties. Imprecise load measurement, or the inability to measure such stresses at all, is another problem that requires over engineering—the safety factor engineers add to compensate for uncertainty. Expensive and potentially lethal machinery, such as aircraft, is routinely retired based on time or operational cycles because the true fatigue within the machine cannot be known.

In all previous load or stress measurement applications, the focus has always been on adding external sensors such as optical or metal foil strain gages. This present invention is novel in that the focus is now on conditions inside the machine or structure: the stresses experienced by structural members and the performance of the machine itself are the issues rather than an estimation of those forces from the output of external sensors. As distinct from Couchman '122, ultrasonic principles are used here to directly measure stresses in load bearing members without regard for the torque on the fastener being used as the sensor. In other words, the present invention is concerned with the change in loads during operation as measured by properly equipped fasteners.

In the system and method of this invention, the change in the stress or load experienced by a structural member and the largest absolute magnitude of that stress is important with the preload torque on a fastener being relevant only for comparison. Such changing loads during operation are commonly referred to as "dynamic".

Piezoelectric equipped or "ultrasonic" fasteners work by transmitting ultrasonic pulses through the fastener from a piezoelectric crystal transducer which is commonly affixed to one end. The time required for the signal to reflect back to said transducer can be analyzed to indicate the fastener's deformation or elongation which is a direct measure of the stress being exerted on that fastener by the structure. Since the fastener is immovably mounted within the structural member, the loads are the same in the fastener as in the structure. Changes in a signal's time of flight are a direct measure of changes in the stress experienced by the associated fastener as well as in the associated structure.

The most common application of the present invention would use piezoelectric equipped fasteners in the entirely different application of direct and active measurement of both static and dynamic stresses. In this context, the term stress measurement refers to measuring the load or stress, and changes in the load or stress, within the fasteners which is a direct indication of conditions and the changes in conditions within the surrounding structure into which said fasteners are installed. It is also possible to install piezoelectric transducers in other suitable load bearing media such as the steel rebar rods used in reinforced concrete. The load or stress measuring method would be substantially the same regardless of which load bearing media is used.

Rather than measuring the elongation of fasteners only for setting or checking torque and fastener integrity, this invention would measure stress at critical points in a structure or machine through those same fasteners. Such stress measurements would be made as required. Some applications, such as bridges, would conceivably be measured intermittently and others, such as aircraft or engines, would more likely be monitored constantly. Known ultrasonic stress measurement technology is herein used for the entirely new purpose of measuring stress, not in a fastener, but in the surrounding member of the structure or machine into which the fastener is fixed. Of course, the conventional application of setting and checking torque is still possible.

Ultrasonic fasteners can also be installed purely as sensors with no connective function at all. This technology also facilitates measuring the load on fittings which are not strictly considered fasteners but which are configured so as to allow ultrasonic measurement of their deformation.

DETAILED DESCRIPTION OF THE INVENTION

This invention concerns a method and associated measuring system that determines loads or stresses within structural members which are in operation and the associated analytical tools necessary to make those measurements useful. Such measurements facilitate enhanced safety, performance monitoring, improved maintenance functions and more efficient designs by actively measuring the stress or load in critical components. Other applications of active stress or load measurement will be apparent to those skilled in several arts such as civil engineering, aviation, transportation, ship building, security, disaster response and architecture.

Figure 1:
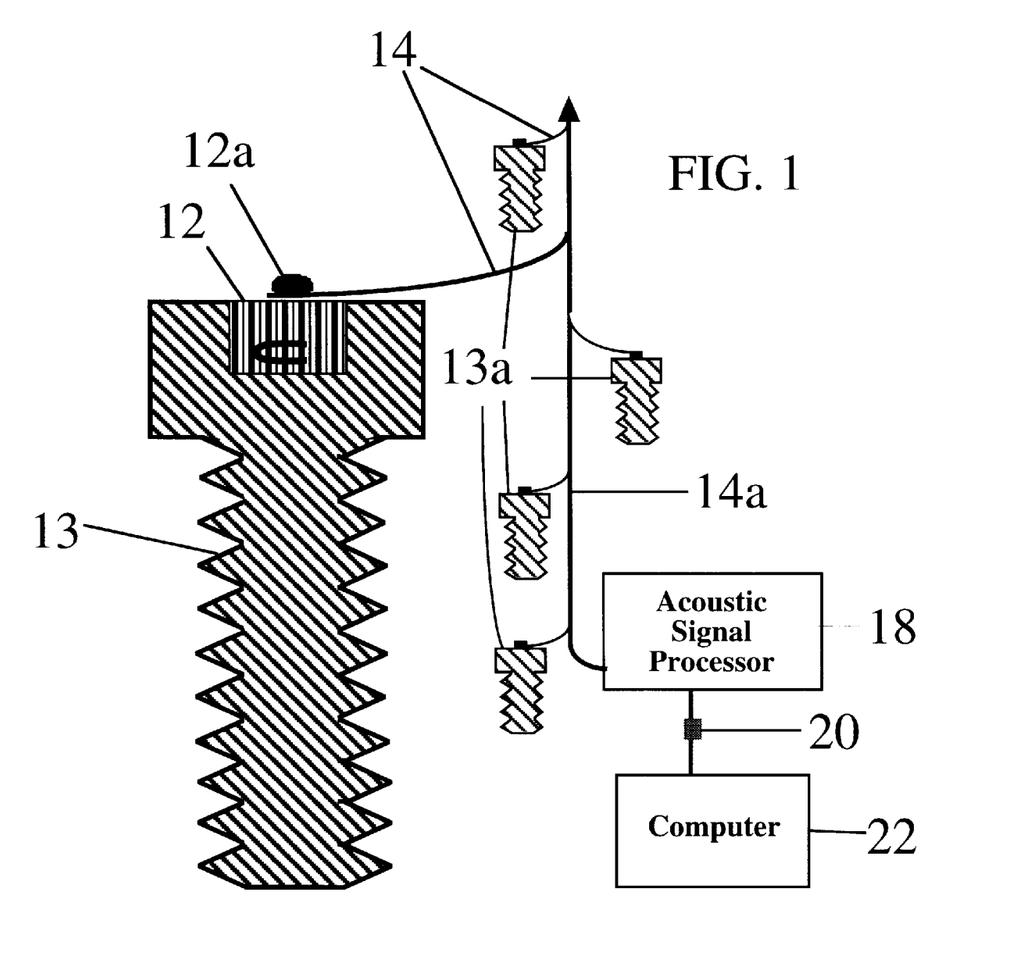
FIG. 1 shows a system of standard fasteners equipped with piezoelectric transducers installed as active sensors in a system of this invention.

This application is facilitated by securely attaching an appropriately designed electrical lead to a piezoelectric crystal or other transducing medium permanently fixed into a fastener (or other element) installed in the load bearing member of an aircraft, machine or structure. When networked, the transducer equipped fasteners form a system of sensors. The analytical tools consist of well known computers, software and connection media linking said network to the information display or other final application. One example configuration is seen in FIG. 1. One preferred embodiment begins with a standard fastener or bolt 13 which may eventually be installed singly or as part of a system of sensors 13a. The bolt must be chosen for its ability to meet the fastening requirements of its intended application if it also serves to form a joint. For this description, generic bolts are depicted since fasteners are made in a wide variety of shapes and the specific shape is not relevant to this invention. The fastener or bolt is equipped with an ultrasonic transducer 12, such as a piezoelectric crystal. Such ultrasonic fasteners are well known in the art of forming joints. Such ultrasonic fasteners may be used to connect structures and bear loads exactly as ordinary fasteners would or they may be installed purely as sensors. In that purely sensing application, an ultrasonic fastener would be installed in a hole drilled or forged and tapped solely for the purpose of installing said sensor.

After installation, the transducer 12 is fixedly connected to a wire 14 with a fastening means 12a. The wire may run singly or in a multiplexed wiring harness 14a to an acoustical signal processors for signal processing. A computer or processing means 22 is, in turn, either temporarily connected through a canon plug or other quick release electronic coupling 20, or permanently connected to the acoustical signal processor 18 for the purpose of monitoring stresses through the equipped fittings. Details of the electrical connections and circuits outlined here are well known in that art. The connections between sensors and processing hardware may be made by wire, coaxial cable, fiber optic, radio or any other suitable transmission medium.

Figure 2:
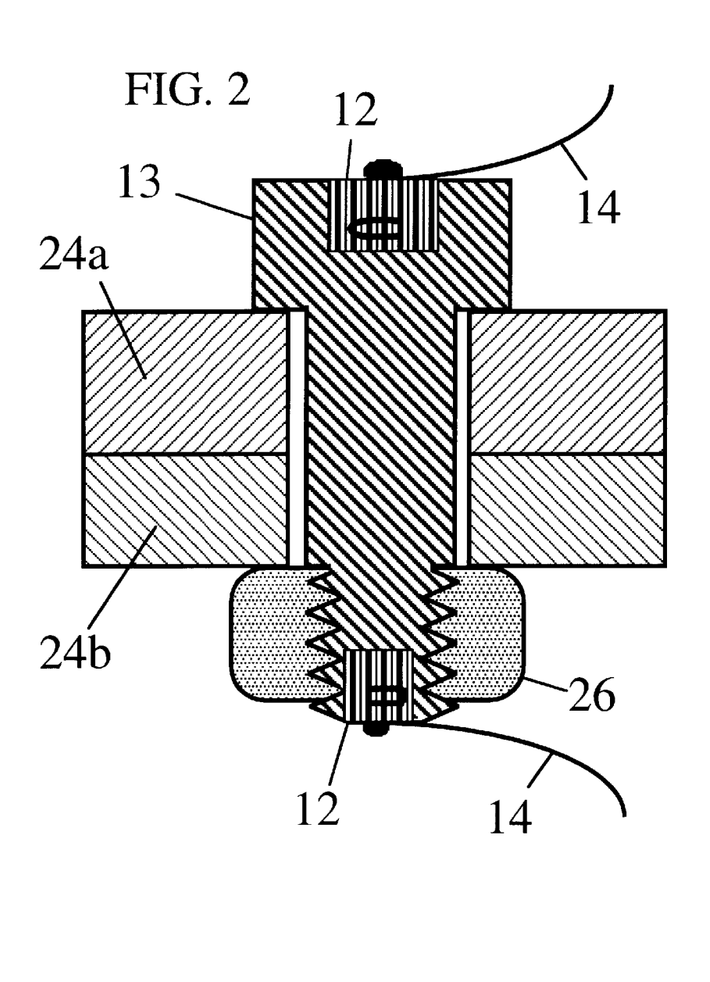
FIG. 2 shows one application of the present invention wherein an ultrasonic fastener is used to join two plates together.

Example modifications of this invention are shown beginning with FIG. 2. FIG. 2 illustrates a transceiver equipped fastener 13 installed between and securing together two plates 24a and 24b of material. The plates of material could be structural members of an aircraft, hull plates on a ship, joined beams in a building or road surface foundation plates on a bridge, for example. The fastener 13 is secured by a conventional nut 26 though other fastening methods such as riveting are apparent. An ultrasonic transducer 12 is attached to a signal transceiver (not shown) by wire 14. When equipped with transducer 12, fastener 13 functions both as a fastener joining said materials and as a sensor. The transducer may be installed into either end of a fitting as is illustrated by the transducer 12 shown at both ends of the fastener 13. Two transducers are shown for illustration of alternate configurations only and are not required by this invention.

Figure 3:
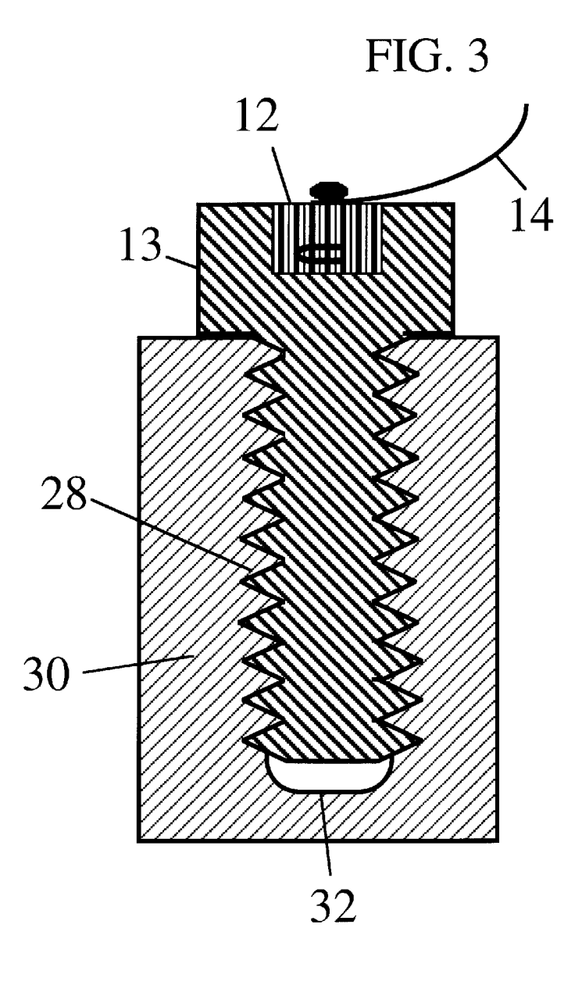
FIG. 3 shows another application of the present invention wherein an ultrasonic fastener is threaded into hole of a structure and serves solely as an active sensor with no fastening function.

Another modification is shown in FIG. 3. FIG. 3 illustrates a transducer equipped fastener 13 installed in a member 30 without serving any fastening function. Fastener 10 could be installed by drilling or forging a hole 32 and then tapping the hole for the fastener's threads 16. Without a fastening function, the fastener-turned-sensor 10 in FIG. 3 functions solely as an active sensor by being immovably locked into member 30 and measuring the stresses within said member 30. As in FIG. 1, fastener 13 is equipped with an ultrasonic transducer 12 which is attached to a signal transceiver (not shown) by an electrical cable 14.

Figure 4:
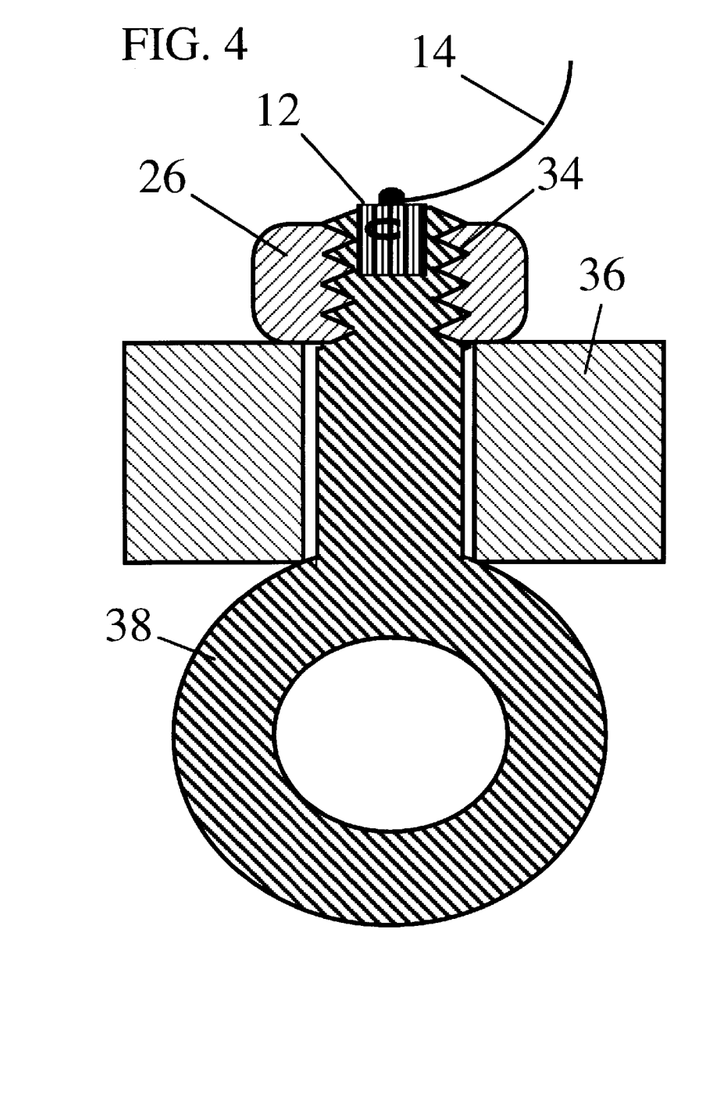
FIG. 4 shows yet another application of the present invention wherein an eyebolt or ring fitting, fitted with a piezoelectric transducer, is used to support loads from the ring portion thereof

FIG. 4 illustrates a further modification of the present invention in the form of a threaded ring fitting 34 typically used in suspension applications such as block and tackle lifts, helicopter slings or cable structural members. This threaded ring fitting 34 is secured by a conventional nut 26 to the supporting member 36. Loads are attached to threaded ring fitting 34 at the ring 38. The active sensing properties of the present invention are facilitated by inclusion of a piezoelectric transducer 12 connected to a signal transceiver (not shown) by an electrical cable 14 in the manner described above for fasteners.

Figure 5:
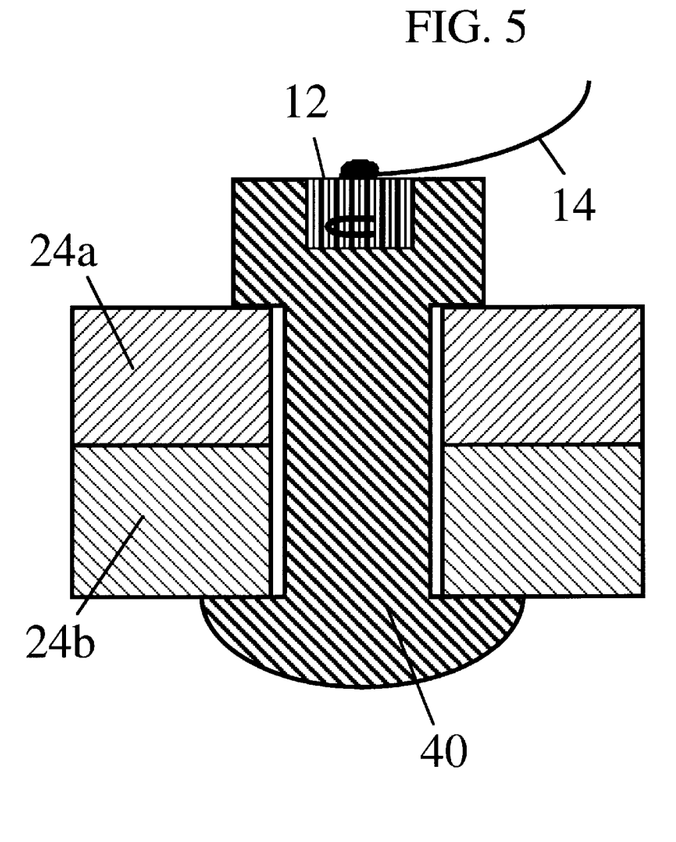
FIG. 5 shows a further application of the present invention wherein a piezoelectric transducer is installed in rivet which forms a joint between two plates of material.

FIG. 5 illustrates yet another modification of the present invention using a non-threaded fastener, rivet 40, converted into this system's sensor. The same or similar piezoelectric transducer 12 is installed in rivet 40 which itself forms a joint between plates of material 24a and 24b. Rivet 40 could also, of course, be installed without a fastening function similar to the arrangement in FIG. 3. Because the exact configuration and function of the fitting-turned-sensor is not restricting, the same connections and controls illustrated in other figures also apply to FIG. 5.

It must be recognized that many other structural fittings can be similarly used as sensors according to this method. If a fitting changes length while its structure is in operation or stressed, and the fitting will propagate ultrasonic signals, it is a candidate for conversion into a sensor.

At intervals specified by the user's requirements, perhaps continuously, the controlling computer or processing means 22 causes ultrasonic pulses to be generated in the relevant piezoelectric transducer 12 and transmitted from that transducer 12 along the fitting into which it is fixed. The resulting return signal is then transmitted back along the electrical connection 14 to computer or processing means 22 which is programmed to interpret the return signal and/or combine it with other similar signals from other fittings into the required load or stress measurement information.

Since a fitting immovably fixed inside a load bearing member experiences exactly the same stresses or loads that are experienced by that member at that point, measurement of the stress or load in said fitting is a direct measurement of the stress in the associated member. By either designing such fittings, such as transceiver equipped fasteners 13, into machinery or retrofitting them into existing designs, and connecting them to devices capable of monitoring the resulting signals, the novel application of directly and actively monitoring the stress or load experienced by structural members is possible.

Figures 6, 7:
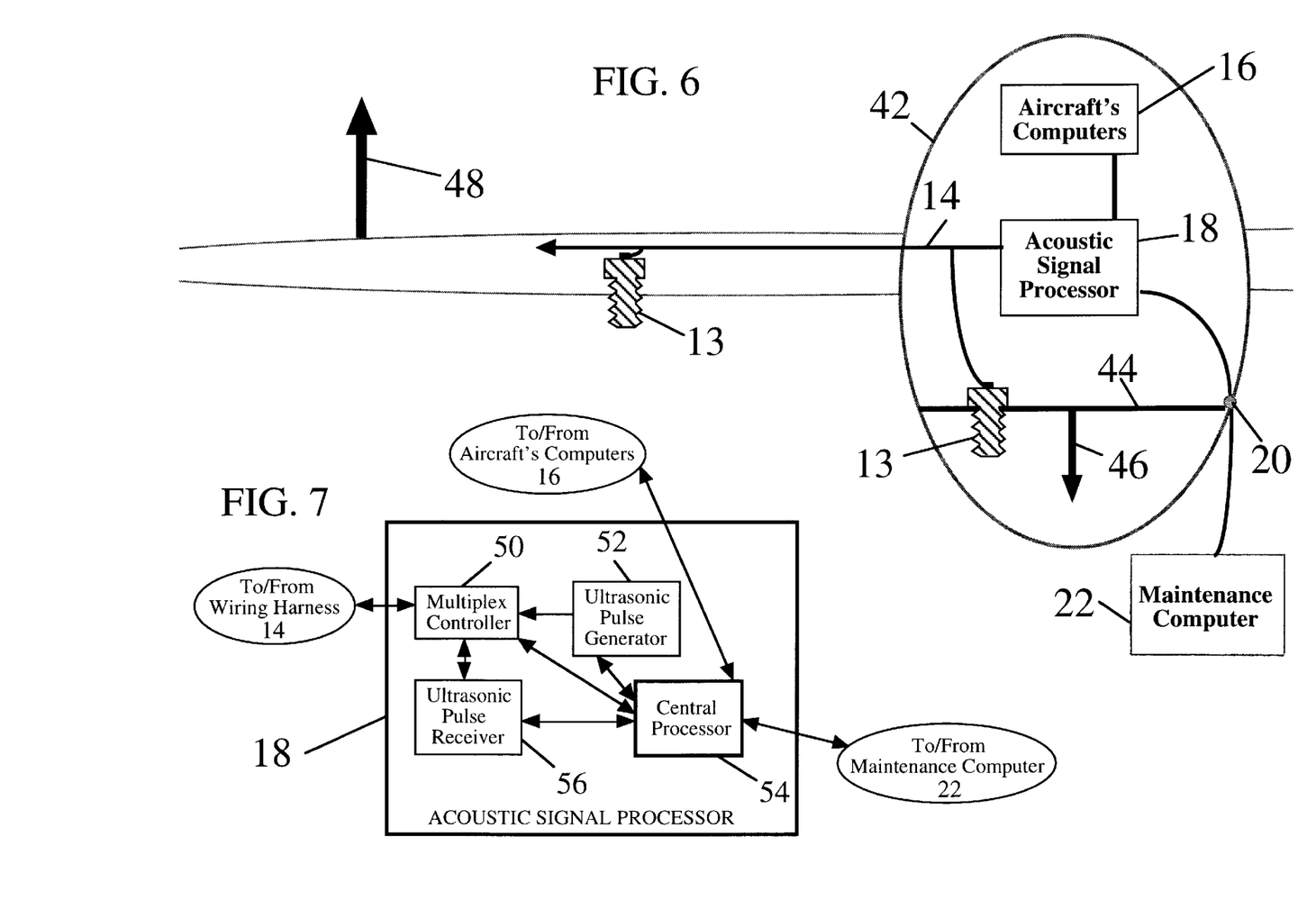
FIG. 6 shows one application of the present invention as applied to an aircraft.
FIG. 7 shows in some detail the acoustic signal processor shown in FIG. 6.
Figure 8:
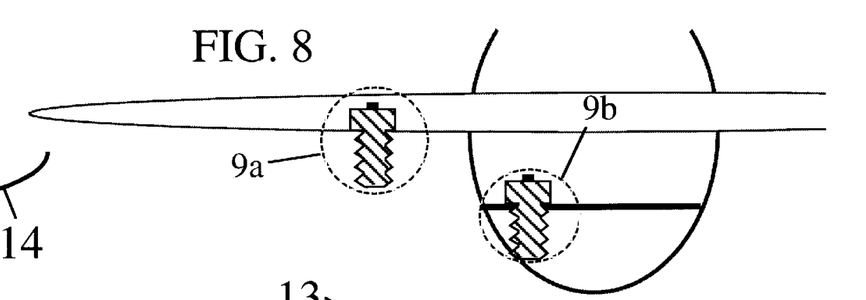
FIG. 8 shows a simpler view of the application shown in FIG. 6.

One practical application of this invention is shown in FIG. 6 as applied to an aircraft 42. A system of standard fasteners 13 equipped with piezoelectric transducers (not shown in this figure) are installed as a system of active sensors at selected locations on the aircraft 42, for example, in the wings and fuselage of the aircraft 42. The aircraft's normal fight and systems management computers are shown at 16. These computers or processing means 16 are connected to an acoustical signal processor 18 which is further detailed in FIG. 7. The acoustical signal processor 18 is connected to piezoelectric equipped fasteners 13 via a multiplexed wiring harness 14a. Alternatively, maintenance capability is provided by portable maintenance testing equipment or processing means 22 which is connected to a processor 18 through port 20 located at any convenient point on the aircraft 42. FIG. 6 further shows a cargo deck 44 and a force vector 46 acting on that deck 44 due to the payload supported by it. Lifting force 48 is shown acting on the wing. Although the application of this invention is shown with a particular type of aircraft, this invention is also applicable to other types of aircraft.

FIG. 7 shows details of one possible embodiment of the acoustical signal processor 18. In this embodiment, there is a Central Processor 54 which communicates with either or both processing means 16 and 22 through any suitable connections. The Central Processor 54 is connected to the pulser or Ultrasonic Pulse Generator 52 and the Multiplex Controller 50 in order to generate an ultrasonic signal in the correct fastener 13 through harness 14a. The return signal passes through the multiplex controller 50 enroute to the Ultrasonic Pulse Receiver 56. The Receiver 56 is connected to the Central Processor 54 which, in turn, routes interpreted stress information to the appropriate processing means for use.

As was previously mentioned, FIGS. 6 and 7 detail one possible embodiment of the present invention. An Acoustic Signal Processor 18 and multiplex wiring harness 14a connect any number of ultrasonic fasteners 13, which may or may not form joints as necessary for aircraft function. Processor 18 is also permanently connected to the aircraft computers or processing means 16 which are common to all modern aircraft and removably connected to maintenance testing equipment or processing means 22. All processing means 16 and 22 are programmed to both command signal processor 18 to interrogate fasteners 13 and incorporate the resulting stress or load information into their required functions.

As was previously noted, Processor 18 is further detailed in FIG. 7. In this particular embodiment, the Central Processor 54 receives commands from either or both processing means 16 and 22 through any suitable connection. As appropriate for the function required by the commanding computer, for example, continuously, Central Processor 54 commands the pulser or Ultrasonic Pulse Generator 52 to generate an ultrasonic signal in the correct fastener 13 through piezoelectric transducer 12. The return signal is identified by the Multiplex Controller 50 and routed to the Ultrasonic Pulse Receiver 56. Receiver 56 interprets the return signal and delivers it the Central Processor 54 which converts the ultrasonic echo information into stress and load information which is useful to the aircraft or maintenance computer. Similar embodiments are clearly evident for other applications.

Figure 9A:
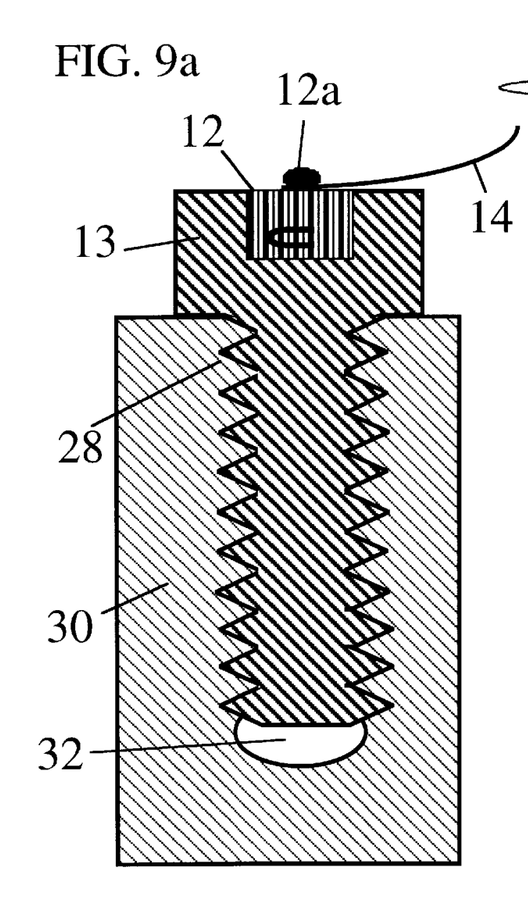
FIG. 9a shows an exploded view of the fastener in the encircled area 9a of FIG. 8.

FIG. 9a shows an ultrasonic fastener 13 installed by its threads 28 into a hole 32 of an aircraft wing; fastener 13 acts solely as an active sensor in structure 30 with no fastening function. The piezoelectric transducer 12 is shown connected to wire 14 by connector 12a. This arrangement illustrates one possible embodiment of the present invention by which stress or load data are generated from a glass fiber composite wing structure which is typically glued with no fasteners.

Figure 9B:
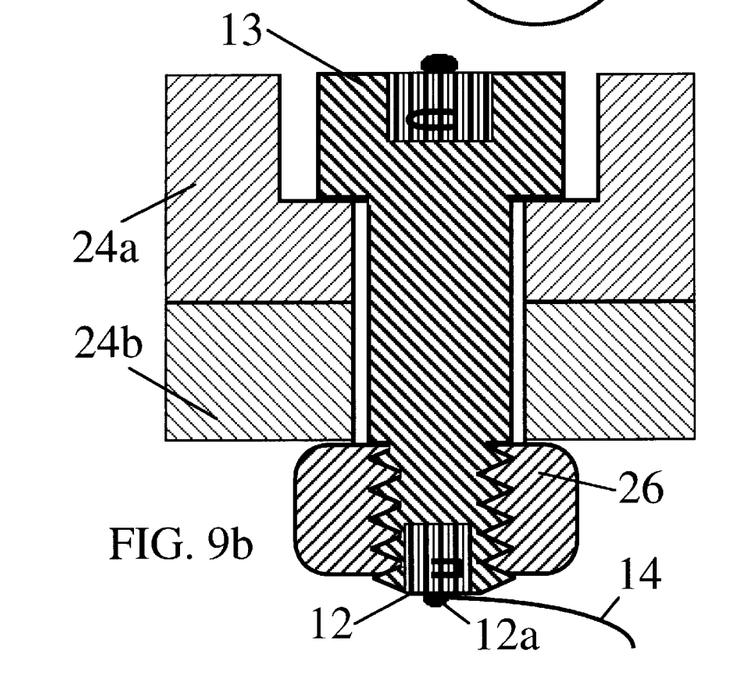
FIG. 9b shows an exploded view of the fastener in the encircled area 9b of FIG. 8.

FIG. 9b shows an ultrasonic fastener 13 flush mounted to join plates 24a and 24b while being secured by a standard nut 26 as would typically be found in a cargo deck 44.

Figure 10:
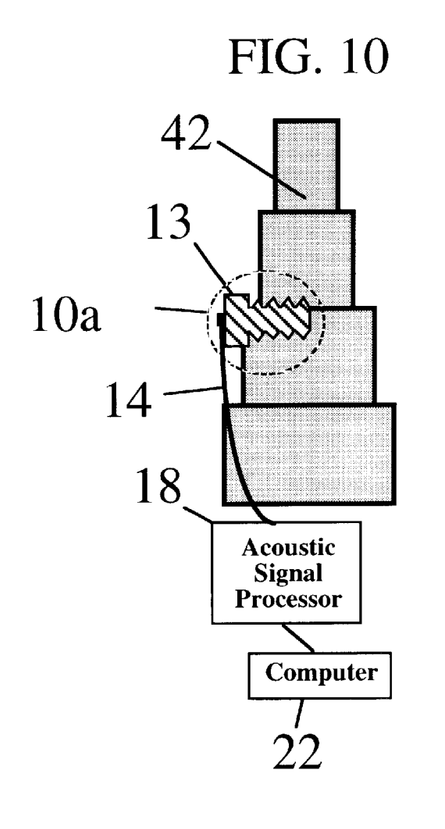
FIG. 10 shows another application of the present invention as applied to a building.
Figure 10A:
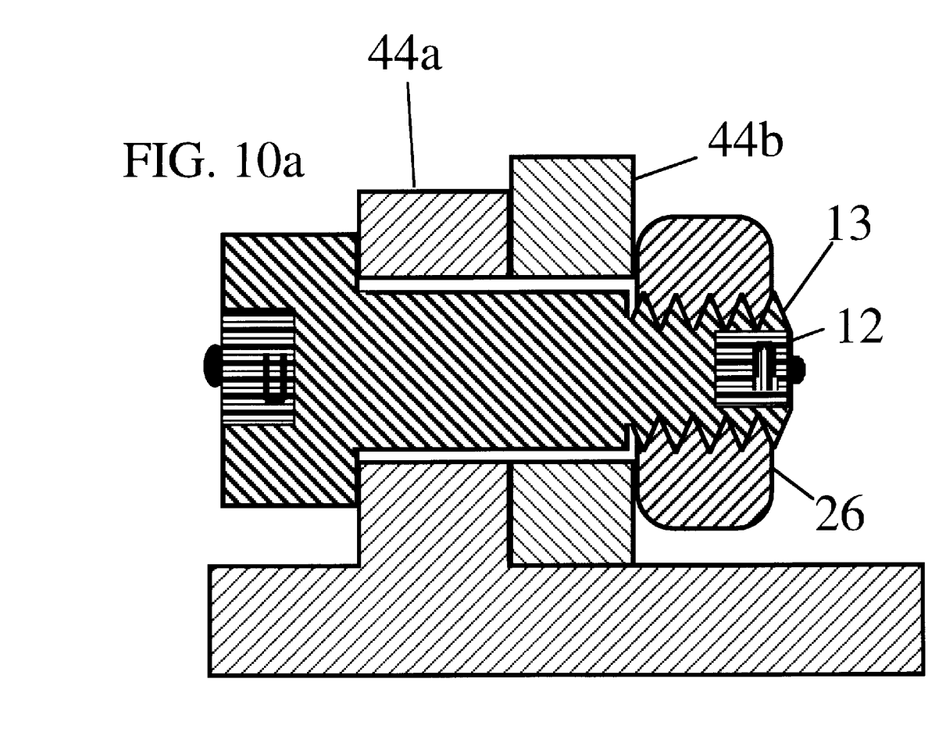
FIG. 10a shows an exploded view of the fastener in the encircled area 10a of FIG. 10.

FIG. 10 shows another application of the present invention in which a fastener 13 (equipped with a piezoelectric transducer 12) is installed in structural members of a tall building 42. FIG. 10a shows an exploded view of that installation. In particular, fastener 13 joins two structural members, here shown as horizontal member with flange 44a and vertical I-beam 44b. As with other applications of the present invention, this application joins members 44a and 44b with fastener 13 and nut 26 while also delivering stress or load information by connecting transducer 12 to the acoustic processing means previously described but not shown in this figure.

Figure 11:
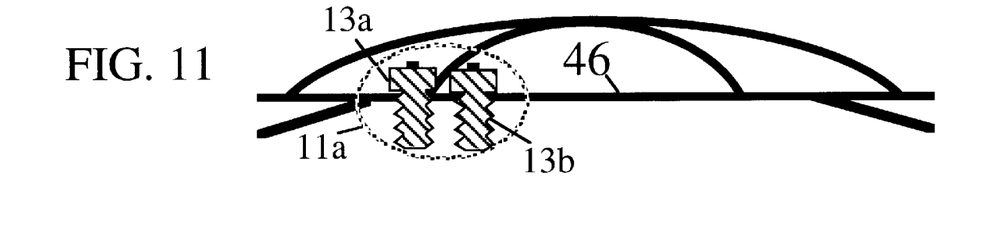
FIG. 11 shows a further application of the present invention as applied to a bridge.
Figure 11A:
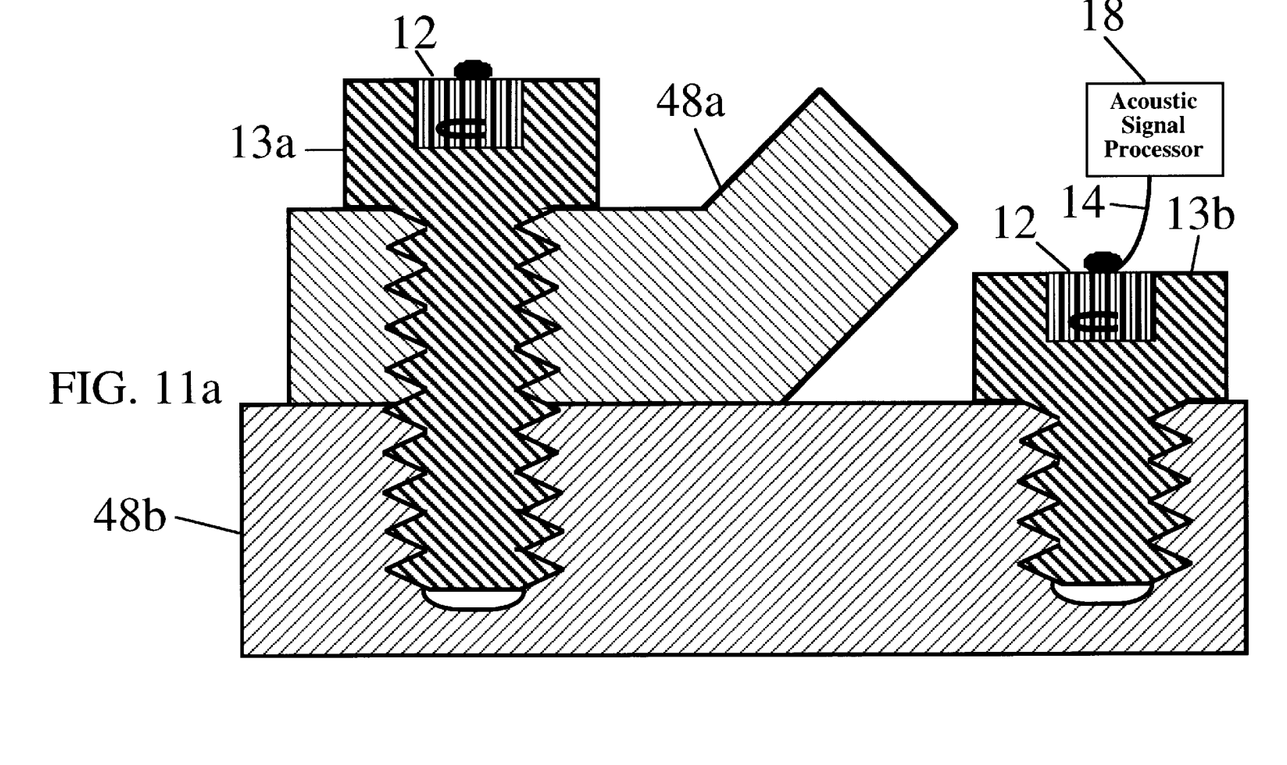
FIG. 11a shows an exploded view of the fastener in the encircled area 11a of FIG. 11.

FIG. 11 shows a further application of the present invention as applied to a bridge 46. FIG. 11a details the installation of fasteners 13a and 13b in two different ways. Fastener 13a forms a joint between bridge structural members 48a and 48b while also equipped with transducer 12 to act as a sensor. Fastener 13b is installed in a bridge structural member 48b and has no joining function. When properly fitted with a transducer 12 and connected to an acoustical signal processor 18 by means of wire 14, fitting or fastener 13b functions solely as an active load or stress sensor according to one feature of this invention.

A primary object of this invention is to cheaply and reliably monitor internal stresses in such applications as, but not limited to:

instantaneous measurement of conditions such as the loads borne by critical structures;

calculation of performance information for the associated structure or machine;

measurement of long term or cumulative stress, such as the intensity and duration of load cycles, that affect the safe useful life of a machine or structure; and measurement of the structural integrity of a machine or structure during and after an event that approaches or exceeds design limits.

Other applications of this invention would be apparent in any industry which uses load bearing structures, in power transfer applications, and in other applications requiring knowledge of loads or stresses. Either when designed-in or retrofitted, a system using the present stress or load measurement method of this invention will allow stress on aircraft wings and engines to be monitored constantly, for example. The present invention installed in a railroad bridge could be linked to standard signaling devices and warn a train's crew to stop if a fault is detected. A network of sensors installed, according to the method of this invention, in buildings, bridges and other structures could be interrogated after an earthquake for a quick damage assessment.

The ability to reliably monitor internal stresses allows the instantaneous measurement of conditions such as loads borne by critical structures.

Using an aircraft example, acceleration or G forces are measured by accelerometers commonly located in the cockpit and wingtips. Such instruments can only precisely measure the force experienced by the instrument itself and are only an accurate approximation for their location within the aircraft. Accelerations in various parts of an aircraft vary with distance from the center of gravity and with the roll rate. The desired information on stresses experienced by structural members, as well as the accelerations experienced in locations remote from an accelerometer, must be estimated. Many aircraft fly with multiple accelerometers in an attempt to reduce these uncertainties. The use of accelerometers in the first place is an approximation necessitated by the fact that acceleration can be measured while it has been previously impossible to directly measure stress. Discerning the stress experienced within the aircraft is the real need that drove the development of accelerometers in the first place. Critical structural members must be over-designed to account for worst case uncertainties and laborious inspections follow any out of limits accelerometer indications to determine what really happened within those critical structural members. Such over design drives severe cost and performance penalties that can be reduced with the use of the present invention. As in this example of possible over stress to an aircraft, information from these proposed active sensors can be used to reduce or eliminate the down time required for non-destructive testing.

The ability to reliably monitor internal stresses allows the calculation of performance information for the associated structure or machine:

Returning to the aircraft example, when an aircraft wing flexes upward as aerodynamic lift increases, fasteners in some parts if its structure are stretched while others are compressed. Measurements of the rate and magnitude of those forces experienced by the fasteners is a measure of performance given the fact that the stresses experienced by the structure are directly proportional to the lift being generated by the wing. Similarly, internal combustion engine head bolts fitted in the method described in this invention would be able to directly measure the stresses caused by the expansion of burning fuel and, thereby, indicate critical performance parameters such as compression ratio and power output, as well as structural load information relative to design limits.

Stress measurements taken as propellant burns would allow fine aiming adjustments to be made as a projectile accelerates along the barrel of an artillery piece.

Stress information from within lifting apparatus such as cranes would indicate both the weight of the load and the safety margin remaining for that operation.

Load information taken from the floor of cargo carriers, such as aircraft, trucks, ships or rail cars, would allow the rapid, automated and accurate completion of weight and balance calculations as well as ensuring that the machine or structure is not loaded beyond its limits.

The ability to reliably monitor internal stresses allows for the measurement of long term or cumulative stress such as the intensity and duration of load cycles that affect the safe useful life of a machine or structure:

The internal stresses on structures, such as the wing box of an aircraft or the trusses within bridges and buildings, can be measured for both safety and maintenance purposes. For example, a bridge could be monitored for both routine stresses caused by traffic and for safety after a high stress event such as an earthquake, collision or flood. The derailment of an Amtrak passenger train from a bridge that had been rammed by a barge could have been avoided if the present invention was installed on that bridge, interrogated occasionally and connected to the railroad's signaling system. Roadway bridges and critical structures, such as hospitals and dams, could be interrogated electronically with wireless links after earthquakes. That information would be useful in directing evacuations, in stopping traffic bound for severed transportation links and in routing rescue services to where they are most needed. The transceiver and sensors system would likely be linked to the computer through a survivable remote link such as battery powered radio in this case.

Measuring structural loads through fasteners installed at critical locations, or through fasteners functioning strictly as sensors, results in information which can then be compared directly to design limits. Such information would, for example, allow the stresses on an aircraft wing to be reduced before exceeding design limits or facilitate focused, efficient, relevant inspections when design limits are exceeded for any reason.

In an internal combustion engine, it will now be possible to automatically cut off the electronic ignition to an engine when a head bolt or connecting rod deforms beyond limits rather than waiting for the next several power strokes to destroy the engine.

With this innovative method, it is possible to compile a record of stress information which would be invaluable in measuring the cumulative fatigue experienced by the associated component. That record would then allow a structure or machine to be used for its full life rather than being retired early, as is now required in aviation for safety, or retired late through errors in estimating its use.

Using the aircraft example again, structural life is now estimated by tracking operational factors such as hours flown or landings made. Given that the stresses experienced by the wings and other structures varies widely with flight variables such as altitude, speed and turbulence, such estimates are marginal at best. Structures must be retired early in order to allow for the inaccuracy of that stress estimation. Landing gear cycles, for another example, are a barely relevant measure of fatigue given the fact that one hard landing causes far more stress than a number of smooth landings. A C-130 airtanker crashed in the early 1990s when it continued to fly with an undetected failure in a wing structure. That wing came off in flight.

The U.S. Air Force replaced the entire wing box (the fuselage structure that attaches wings to aircraft) on 50 Lockheed C-5A Galaxies because engineering analysis indicated that the original structure could not bear the required loads for the planned useful life. There was no way to measure the relevant stresses directly so safety demanded that extremely expensive precautionary retrofit. The direct measurement method of this invention would have provided the relevant stress data needed in that situation.

Power transfer systems will benefit from the accurate stress information available with this proposed invention. Power generating systems must be designed to bear severe loads for long periods. Electricity generating machinery operates at high constant stress and would benefit from the availability of stress and fatigue measurements taken while the machinery is in operation. Powerful machinery, such as earth moving equipment and armored vehicles, operate with repeated power transfer cycles that cause rapid transmission fatigue and which require significant over-design. Such machinery could be operated more efficiently with this stress or load measuring method facilitating real time comparison of operating stress to design limits. Common transmission failures in said machinery would be avoided by connecting the stress analysis computer 22 to the engine's governor or other control system.

The measuring medium does not have to be a fastener. Ultrasonic transducers, fitted on the ends of rebars, during construction could be used to monitor the integrity of concrete structures and roadways. Piezoelectric transducer equipped fasteners used in other parts of such constructions would also deliver dynamic load information.

With the new methods derived from this invention, stress or fatigue information could be displayed as warnings to the operators, used to automatically inhibit actions which would stress the subject aircraft, machine or structure beyond its design limits and/or be automatically passed to the organizations charged with the maintenance and safety of the aircraft, machine or structure.

Given the fact that cracks and other abnormalities alter internal stresses and stress transmission within structural members, use of ultrasonic fasteners would also reduce the need for expensive and time consuming non-destructive inspections of the associated structures. Such inspections could be performed in a very short time by interrogating the fasteners while the structure is at rest with out of limits changes in the preload stress or torque indicating the need for more detailed inspection. Such inspections could be performed on a routine basis or after an event such as a hard landing experienced by an aircraft or an earthquake experienced by a structure.

While the invention has been particularly shown and described with reference to preferred embodiments thereof, it will be understood by those skilled in the art that various changes and modifications in form and detail may be made thereof without departing from the sprit and scope of the invention.

EFFICACY

The principles of this invention have been proven through experiments conducted and documented at the Sandia National Laboratory in Albuquerque, N. Mex. Investigators at the Sandia National Laboratory varied the intensity and duration of loads applied to a cantilever structure and were able to measure the characteristics of those loads through a bolt modified as detailed in this specification.

What is claimed is:

1. In combination, an aircraft and a system for measuring dynamic stresses in the structure of said aircraft, said aircraft comprising a fuselage and a pair of wings attached thereto, said system comprising a plurality of fixed elements embedded in predetermined locations of said fuselage and said wings, an ultrasonic or acoustical sensor attached to each of said elements, an acoustical signal processing means, a transmission means connected between each of said ultrasonic or acoustical sensors and said acoustical signal processor wherefrom ultrasonic pulses are transmitted to each of said fixed elements through said attached ultrasonic or acoustical sensor and back to said acoustical signal processing means which, in turn, is connected to a computer programmed to convert said returned ultrasonic pulses into stress measurement information.

2. The combination of claim 1 wherein said ultrasonic sensor is a piezoelectric crystal.

3. The combination of claim 1 wherein each of said plurality of elements is a fastener.

4. The combination of claim 3 wherein said fastener is threaded.

5. The combination of claim 1, wherein said acoustical signal processing means comprises a central processor, an ultrasonic pulse generator, an ultrasonic pulse receiver and a multiplex controller, said central processor controlling the operation of each of said ultrasonic pulse generator, said ultrasonic pulse receiver and said multiplex controller, said ultrasonic pulse generator and said ultrasonic pulse receiver being electrically connected to said multiplex controller, and said multiplex controller being electrically connected to said transmission means for sending and receiving acoustical signals to respective ones of said plurality of fixed elements.

6. The combination of claim 5, wherein said acoustical signal processing means is connected to a fixed, computer in said aircraft.

7. The combination of claim 5, wherein said acoustical signal processing means is connected to a mobile maintenance computer.

8. The combination of claim 1, wherein said stresses are measured and monitored constantly by said system during operation of said aircraft.

9. In combination, a machine or static structure and a system for measuring stresses in predetermined locations of said machine or structure, said system comprising a plurality of fixed elements embedded in said predetermined locations of said machine or structure, an ultrasonic or acoustical transceiver attached to each of said elements, an acoustical signal processing means, a transmission means connected between each of said ultrasonic or acoustical transceivers and said acoustical signal processing means wherefrom ultrasonic pulses are transmitted to each of said fixed elements through said attached ultrasonic or acoustical transceiver and back to said acoustical signal processing means which, in turn, is connected to a computer programmed to convert said returned ultrasonic pulses into stress measurement information.

10. The combination of claim 9 wherein said ultrasonic transceiver is a piezoelectric crystal.

11. The combination of claim 9 wherein each of said plurality of elements is a fastener.

12. The combination of claim 11 wherein said fastener is threaded.

13. The combination of claim 9 wherein some of said plurality of elements are non-threaded.

14. The combination of claim 9, wherein said acoustical signal processing means comprises a central processor, an ultrasonic pulse generator, an ultrasonic pulse receiver and a multiplex controller, said central processor controlling the operation of each of said ultrasonic pulse generator, said ultrasonic pulse receiver and said multiplex controller, said ultrasonic pulse generator and said ultrasonic pulse receiver being electrically connected to said multiplex controller, and said multiplex controller being electrically connected to said transmission means for sending and receiving acoustical signals to respective ones of said plurality of fixed elements.

15. The combination of claim 9, wherein said stresses are measured and monitored constantly by said system.

16. A method for measuring stresses at predetermined locations of a structure under load conditions, said method comprising the steps of:

providing a plurality of fixed elements within said structure at said predetermined locations, providing an ultrasonic or acoustical transducer in each of said elements, providing a transmission means, an acoustical signal processing means and a programmed computer, electrically connecting said transmission means between each of said ultrasonic or acoustical transducers and said acoustical signal processing means, electrically connecting said acoustical signal processing means to said programmed computer, generating and transmitting ultrasonic pulses from said acoustical signal processing means to each of said ultrasonic or acoustical transducers to provide an acoustical response signal from each of said elements, receiving each of said acoustical response signals at said acoustical signal processing means, and converting each of said acoustical response signals into stress measurement information by said programmed computer.

17. The method of claim 16 wherein each of said ultrasonic or acoustical transducers is a piezoelectric crystal.

18. The method of claim 16 wherein each of said plurality of elements is a fastener.

19. The method of claim 16 further comprising measuring said stresses more often than once per second while the machine or structure is in operation.

20. In combination, an aircraft and a system for measuring dynamic stresses in the structure of said aircraft, said aircraft comprising a fuselage and at least one lifting device, said system comprising a plurality of fixed elements embedded in predetermined locations of said aircraft, an ultrasonic or acoustical transducer attached to each of said elements, an acoustical signal processing means, a transmission means connected between each of said ultrasonic or acoustical transducers and said acoustical signal processing means wherefrom ultrasonic pulses are transmitted to each of said fixed elements through said attached ultrasonic or acoustical transducer and back to said acoustical signal processing means which, in turn, is connected to a computer programmed to convert said returned ultrasonic pulses into stress measurement information.

* * * * *